United States Patent
Ikehara et al.

(10) Patent No.: US 10,939,681 B2
(45) Date of Patent: Mar. 9, 2021

(54) TETRAZOLINONE COMPOUND AND USE THEREOF

(71) Applicant: SUMITOMO CHEMICAL COMPANY, LIMITED, Tokyo (JP)

(72) Inventors: Takashi Ikehara, Oita (JP); Norio Kimura, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/645,989

(22) PCT Filed: Sep. 10, 2018

(86) PCT No.: PCT/JP2018/033385
§ 371 (c)(1),
(2) Date: Mar. 10, 2020

(87) PCT Pub. No.: WO2019/050026
PCT Pub. Date: Mar. 14, 2019

(65) Prior Publication Data
US 2020/0275659 A1    Sep. 3, 2020

(30) Foreign Application Priority Data

Sep. 11, 2017 (JP) .............................. JP2017-173778

(51) Int. Cl.
*A01N 43/713* (2006.01)
*C07D 403/14* (2006.01)

(52) U.S. Cl.
CPC ......... *A01N 43/713* (2013.01); *C07D 403/14* (2013.01)

(58) Field of Classification Search
None
See application file for complete search history.

(56) References Cited

U.S. PATENT DOCUMENTS

| | | | |
|---|---|---|---|
| 6,642,379 B1 | 11/2003 | Furuya et al. | |
| 2015/0051171 A1 | 2/2015 | Yoshimoto et al. | |
| 2016/0270399 A1 | 9/2016 | Arimori | |

FOREIGN PATENT DOCUMENTS

| | | |
|---|---|---|
| JP | 11-508257 A | 7/1999 |
| JP | 2001-64268 A | 3/2001 |
| JP | 2014-80415 A | 5/2014 |
| WO | WO 97/00612 A1 | 1/1997 |
| WO | WO 99/07687 A1 | 2/1999 |
| WO | WO 2015/056806 A1 | 4/2015 |
| WO | WO 2018/097318 A1 | 5/2018 |

OTHER PUBLICATIONS

English translation of the International Search Report (Form PCT/ISA/210) for International Application No. PCT/JP2018/033385, dated Oct. 30, 2018.
International Preliminary Report on Patentability and English translation of the Written Opinion of the International Searching Authority (Forms PCT/IB/373, and PCT/ISA/237) for International Application No. PCT/JP2018/033385, dated Mar. 17, 2020.

*Primary Examiner* — Abigail Vanhorn
*Assistant Examiner* — Ali S Saeed
(74) *Attorney, Agent, or Firm* — Birch, Stewart, Kolasch & Birch, LLP

(57) ABSTRACT

The present invention provides a compound having excellent control efficacy against pests, especially Lepidoptera pests. A compound represented by formula (1)

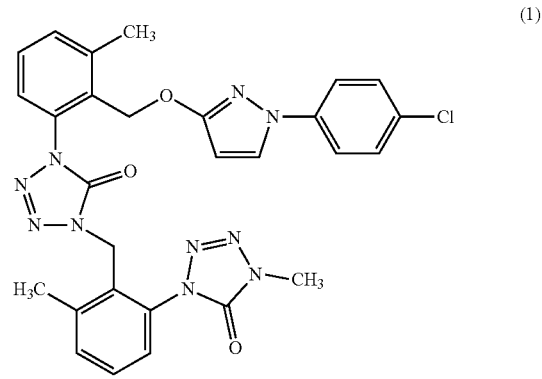

has excellent control efficacy against pests, especially Lepidoptera pests.

3 Claims, No Drawings

TETRAZOLINONE COMPOUND AND USE THEREOF

TECHNICAL FIELD

This application claims priority to and the benefits of Japanese Patent Application No. 2017-173778 filed on Sep. 11, 2017, the entire contents of which are incorporated herein by reference.

The present invention relates to a tetrazolinone compound and use thereof.

BACKGROUND ART

To date, various compounds for controlling pests have been developed and come into practical use. However, a new compound having control activities against pests has been desired due to the pests' development of resistance and the like.

Patent Document 1 discloses tetrazolinone compounds having control effects against pests.

CITATION LIST

Patent Document

Patent Document 1: WO 2015/056806 pamphlet

SUMMARY OF THE INVENTION

Problems to be Solved by Invention

An object of the present invention is to provide a compound having excellent control efficacy against pests, especially Lepidoptera pests.

Means to Solve Problems

The present inventors have studied to find out a compound having excellent control efficacy against pests, especially Lepidoptera pests. As a result, they have found out that a compound represented by the following formula (1) has excellent control efficacy against pests, especially Lepidoptera pests.

That is, the present invention provides the followings.
[1] A compound represented by formula (1)

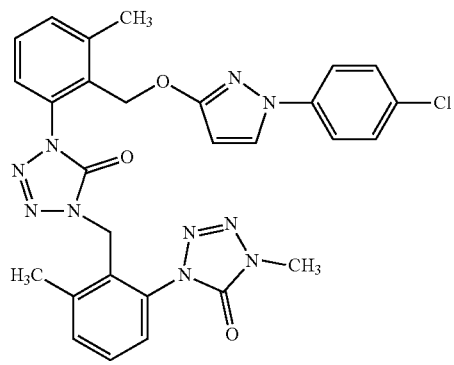

(hereinafter referred to as "Present compound").
[2] An agent for controlling a pest comprising the Present compound (hereinafter referred to as "Present control agent").
[3] A method for controlling a pest which comprises applying an effective amount of the Present compound to a pest or a habitat where a pest lives.
[4] Use of the Present compound for controlling a pest.

Effect of Invention

According to the present invention, pests, especially Lepidoptera pests can be controlled.

MODE FOR CARRYING OUT THE INVENTION

The Present compound is usually mixed with inert carrier(s) such as solid carrier(s), liquid carrier(s) (for example, oil(s)), and gaseous carrier(s), surfactant(s), and/or the others, and as needed auxiliary agent(s) for formulation such as binder(s), dispersant(s), colorant(s), and stabilizer(s) is/are added thereto to be formulated into and used as the Present control agent such as a wettable powder, a granular wettable powder, a flowable, a granule, a dry flowable, an emulsifiable concentrate, an aqueous solution, an oil solution, a smoking agent, an aerosol, and a microcapsule. These formulations usually comprise 0.1 to 99%, preferably 0.2 to 90% by weight of the Present compound.

The Present compound may be mixed with or used in combination with fungicide(s), other insecticide(s), herbicide(s), or the others. Also, potentiation of its effects can be expected by such mixing or using in combination.

Further, the Present compound may be mixed with or used in combination with a compound such as anthraquinone used as a bird repellent.

Examples of the solid carrier to be used in the formulation include fine powders and granules of clays (for example, kaolin clay, diatomaceous earth, bentonite, Fubasami clay, or acid white clay), synthetic hydrated silicon oxides, talcs, ceramics, other inorganic minerals (for example, sericite, quartz, sulfur, active carbon, calcium carbonate, or hydrated silica), chemical fertilizers (for example, ammonium sulfate, ammonium phosphate, ammonium nitrate, urea, or ammonium chloride), and the others; as well as synthetic resins (for example, polyester resins such as polypropylene, polyacrylonitrile, polymethylmethacrylate, and polyethylene terephthalate; nylon resins such as nylon-6, nylon-11, and nylon-66; polyamide resins; polyvinyl chloride, polyvinylidene chloride, vinyl chloride-propylene copolymers, or the others).

Examples of the liquid carrier include water; alcohols (for example, methanol, ethanol, isopropyl alcohol, butanol, hexanol, benzyl alcohol, ethylene glycol, propylene glycol, or phenoxy ethanol); ketones (for example, acetone, methyl ethyl ketone, or cyclohexanone); aromatic hydrocarbons (for example, toluene, xylene, ethylbenzene, dodecylbenzene, phenyl xylyl ethane, or methylnaphthalene); aliphatic hydrocarbons (for example, hexane, cyclohexane, kerosene, or light oil); esters (for example, ethyl acetate, butyl acetate, isopropyl myristate, ethyl oleate, diisopropyl adipate, diisobutyl adipate, or propylene glycol monomethyl ether acetate); nitriles (for example, acetonitrile or isobutyronitrile); ethers (for example, diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, or 3-methoxy-3-methyl-1-butanol); acid amides (for example, N,N-dimethylformamide or N,N-dimethylacetamide); halogenated hydrocarbons (for example, dichloromethane, trichloroethane, or carbon tetrachloride); sulfoxides (for example, dimethyl sulfoxide); propylene carbonate; and vegetable oils (for example, soybean oil or cottonseed oil).

Examples of the gaseous carrier include fluorocarbon, butane gas, LPG (liquefied petroleum gas), dimethyl ether, and carbon dioxide.

Examples of the surfactant include nonionic surfactants such as polyoxyethylene alkyl ethers, polyoxyethylene alkyl aryl ethers, and polyethylene glycol fatty acid esters; and anionic surfactants such as alkyl sulfonates, alkylbenzene sulfonates, and alkyl sulfates.

Examples of the other auxiliary agent for formulation include binders, dispersants, colorants, and stabilizers. Specific examples thereof include casein, gelatin, saccharides (for example, starch, gum arabic, cellulose derivatives, or alginic acid), lignin derivatives, bentonite, water-soluble synthetic polymers (for example, polyvinyl alcohol, polyvinyl pyrrolidone, or polyacrylic acids), PAP (acidic isopropyl phosphate), BHT (2,6-di-tert-butyl-4-methylphenol), and BHA (a mixture of 2-tert-butyl-4-methoxyphenol and 3-tert-butyl-4-methoxyphenol).

The control method of the present invention may be used in controlling pests, especially Lepidoptera pests in croplands such as fields, paddy fields, grasses, and orchards.

Specific examples of the pests, especially Lepidoptera pests which can be controlled by the control method of the present invention include, but are not limited to, the followings.

Lepidoptera Pest:

Pyralidae, for example, rice stem borer (*Chilo suppressalis*), Darkheaded stm borer (*Chilo polychrysus*), *Tryporyza incertulas*, white stem borer (*Scirpophaga innotata*), Yellow stem borer (*Scirpophaga incertulas*), Pink borer (*Sesamia inferens*), *Rupela albinella*, rice leaf roller (*Cnaphalocrocis medinalis*), *Marasmia patnalis*, *Marasmia exigna*, cotton leaf roller (*Notarcha derogata*), mealworm moth (*Plodia interpunctella*), corn borer (*Ostrinia furnacalis*), cabbage webworm (*Hellula undalis*), bluegrass webworm (*Pediasia teterrellus*), rice case-worm (*Nymphula depunctalis*), *Marasmia* spp., Hop vine borer (*Hydraecia immanis*), European corn borer (*Ostrinia nubilalis*), Lesser cornstalk borer (*Elasmopalpus lignosellus*), Bean Shoot Borer (*Epinotia aporema*), Sugarcane borer (*Diatraea saccharalis*), and Giant Sugarcane borer (*Telchin licus*);

Noctuidae, for example, cotton worm (*Spodoptera litura*), beet armyworm (*Spodoptera exigua*), rice armyworm (*Pseudaletia separata*), cabbage moth (*Mamestra brassicae*), pink borer (*Sesamia inferens*), grass armyworm (*Spodoptera mauritia*), *Spodoptera frugiperda*, *Spodoptera exempta*, black cutworm (*Agrotis ipsilon*), beet worm (*Plasia nigrisigna*), Soybean looper (*Pseudoplusia includens*), *Trichoplusia* spp., *Heliothis* spp. (such as tobacco budworm (*Heliothis virescens*)), *Helicoverpa* spp. (such as tobacco budworm (*Helicoverpa armigera*)), Velvetbean caterpillar (*Anticarsia gammatalis*), and Cotton leafworm (*Alabama argillacea*);

Pieridae, for example, common cabbage worm (*Pieris rapae*);

Tortricidae, for example, *Adoxophyes* spp., oriental fruit moth (*Grapholita molesta*), soybean moth (*Leguminivora glycinivorella*), *Matsumuraeses azukivora*, summer fruit *tortrix* (*Adoxophyes orana fasciata*), smaller tea *tortrix* (*Adoxophyes honmai*), Japanese tea *tortrix* (*Homona magnanima*), apple *tortrix* (*Archips fuscocupreanus*), and codling moth (*Cydia pomonella*);

Gracillariidae, for example, tea leaf roller (*Caloptilia theivora*) and Asiatic apple leaf miner (*Phyllonorycter ringoneella*);

Carposinidae, for example, peach fruit moth (*Carposina niponensis*) and Citrus fruit borer (*Ecdytolopha aurantiana*);

Lyonetiidae, for example, Coffee Leaf miner (*Leucoptera coffeela*) and *Lyonetia* spp.;

Lymantriidae, for example, *Lymantria* spp. and *Euproctis* spp.;

Yponomeutidae, for example, diamondback moth (*Plutella xylostella*);

Gelechiidae, for example, pink bollworm (*Pectinophora gossypiella*) and potato moth (*Phthorimaea operculella*);

Arctiidae, for example, American white moth (*Hyphantria cunea*);

and the others.

The target pests to be controlled may have reduced agent-sensitivity or developed agent-resistance.

The control method of the present invention comprises applying an effective amount of the Present compound to pests directly or habitats where pests live (for example, plants, soil, interiors of houses, or animal bodies).

In the control method of the present invention, while the Present compound may be used by itself, it is usually formulated as the Present control agent, and as needed, diluted to be used.

When the Present control agent is used for controlling pests in an agricultural field, the application dose as an amount of the Present compound is usually within the range from 1 to 10,000 g per 10,000 m². When the Present control agent is an emulsifiable concentrate, a wettable powder, or a flowable, it is usually applied by diluting it with water in such a way that a concentration of the Present compound is within a range from 0.01 to 10,000 ppm.

The Present control agent or a diluted solution of the Present control agent with water may be applied not only to habitats where pests live, but also to subjects (i.e., plants, soil, or animals) to be protected from pests.

EXAMPLES

The following Preparation Example, Formulation Examples, and Test Example serve to more specifically illustrate the present invention, but the present invention is not limited to these examples only.

First, a Preparation Example of the Present compound is shown below.

Preparation Example

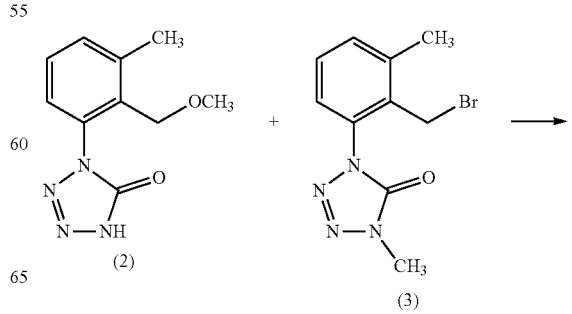

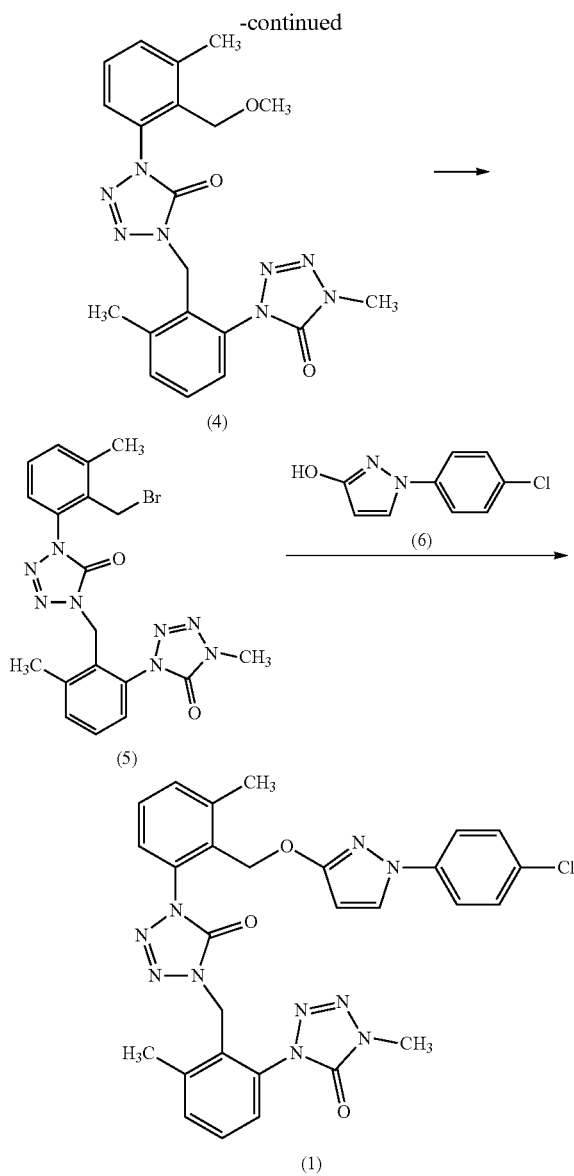

(Step 1)

Under nitrogen atmosphere, a compound represented by formula (2) (41.0 g), potassium carbonate (77.4 g), and acetone (250.0 g) were mixed at room temperature, and the resulting mixture was cooled to 5° C. To the mixture was added a compound represented by formula (3) (50.0 g), the resulting mixture was warmed to room temperature, and then stirred for 21 hours. Then, the reaction mixture was concentrated under reduced pressure to remove acetone by distillation. To the resulting solids were added water (349.5 g) and ethyl acetate (350.5 g), the resulting insoluble matters were removed by filtration, and the resulting mixture was separated. The resulting organic layer was washed with water (349.5 g), and concentrated under reduced pressure to remove solvents by distillation. The resulting solids were washed sequentially with water (1200.0 g) and hexane (251.0 g), and dried under reduced pressure at 40° C. to give a compound represented by formula (4) (49.5 g) (LC area percentage: 99.5%).

(Step 2)

Under nitrogen atmosphere, the compound represented by formula (4) (48.3 g) and xylene (237.0 g) were mixed at room temperature. The resulting mixture was warmed to 40° C., then a 33% solution of HBr in acetic acid (88.8 g) was added dropwise thereto over 2 hours, and the resulting mixture was stirred at 40° C. for 9 hours. Then, to the reaction mixture was added water (97.4 g), and the resulting solids were separated by filtration. The resulting solids were washed sequentially with water (100.3 g), a 5% aqueous solution of sodium hydrogen carbonate (103.4 g), water (293.0 g), and hexane (151.2 g), and dried under reduced pressure at 40° C. to give a compound represented by formula (5) (48.2 g) (LC area percentage: 98.5%).

(Step 3)

Under nitrogen atmosphere, the compound represented by formula (5) (47.2 g), acetone (232.5 g), potassium carbonate (43.1 g), a compound represented by formula (6) (20.1 g), and water (0.7 g) were mixed at room temperature, the resulting mixture was warmed to 50° C., and then stirred for 3 hours. Then, the reaction mixture was concentrated under reduced pressure to remove acetone by distillation. To the resulting solids were added water (235.1 g) and ethyl acetate (234.3 g), and the resulting mixture was separated. The resulting organic layer was washed sequentially with water (234.9 g), water (236.3 g), and water (236.3 g), and the resulting organic layer was concentrated under reduced pressure to give a crude product (60.2 g). The product was purified by silica gel column chromatography (hexane/ethyl acetate), and then subjected to recrystallization by using isopropyl alcohol (422.2 g) to give the Present compound (43.5 g) (LC area percentage: 99.4%).

Present Compound $^1$H-NMR (CDCl$_3$) δ (ppm): 7.61 (1H, d, J=2.4 Hz), 7.51-7.48 (2H, m), 7.40-7.33 (6H, m), 7.23-7.20 (2H, m), 5.77 (1H, d, J=2.4 Hz), 5.25 (2H, s), 5.16 (2H, s), 3.66 (3H, s), 2.62 (3H, s), 2.53 (3H, s)

Next, Formulation Examples of the Present compound are shown below. The "part(s)" represents "part(s) by weight".

Formulation Example 1

The Present compound (10 parts) is mixed with a mixture of xylene (35 parts) and N,N-dimethylformamide (35 parts), and then polyoxyethylene styryl phenyl ether (14 parts) and calcium dodecylbenzene sulfonate (6 parts) are added thereto, followed by mixing them to obtain a formulation.

Formulation Example 2

Sodium lauryl sulfate (4 parts), calcium lignin sulfonate (2 parts), synthetic hydrated silicon oxide fine powder (20 parts), and diatomaceous earth (54 parts) are mixed, and further the Present compound (20 parts) is added thereto, followed by mixing them to obtain a formulation.

Formulation Example 3

To the Present compound (2 parts) are added synthetic hydrated silicon oxide fine powder (1 part), calcium lignin sulfonate (2 parts), bentonite (30 parts), and kaolin clay (65 parts), followed by mixing them to obtain a mixture. To the mixture is then added an appropriate amount of water, the resulting mixture is additionally stirred, and subjected to granulation with a granulator and forced-air drying to obtain a granule.

Formulation Example 4

The Present compound (1 part) is mixed with an appropriate amount of acetone, and then synthetic hydrated silicon oxide fine powder (5 parts), acidic isopropyl phosphate (0.3 part), and kaolin clay (93.7 parts) are added thereto, followed by mixing with stirring thoroughly and removal of acetone from the mixture by evaporation to obtain a formulation.

Formulation Example 5

The Present compound (0.1 part) is mixed with a mixture of xylene (5 parts) and trichloroethane (5 parts), and the resulting mixture is then mixed with kerosene (89.9 parts) to obtain an oil solution.

Formulation Example 6

The Present compound (10 parts), a mixture of polyoxyethylene alkyl ether sulfate ammonium salt and wet silica (weight ratio of 1:1) (35 parts), and water (55 parts) are mixed, and the resulting mixture is finely ground by a wet grinding method to obtain a formulation.

Next, a Test Example is used to show efficacy of the Present compound against pests. In the following Test Example, the test was carried out at 25° C.

Test Example 1 Control Test Against Diamondback Moth (*Plutella xylostella*)

The Present compound was formulated according to the process described in the Formulation Example 6 to obtain a formulation, and water containing a spreader (0.03% by volume) was added thereto to prepare a diluted solution containing 500 ppm of the active ingredient.

Cabbage (*Brassicae oleracea*) seedlings (on the developmental stage of the second to third true leaf) were planted in a container, and said diluted solution was sprayed into the leaves of the seedlings at a ratio of 20 mL/seedling. Thereafter, the stems and leaves of the seedlings were cut out, and the leaves were placed into a container lined with a filter paper. Approximately five the 2nd instar larvae of diamondback moth (*Plutella xylostella*) were released into the container. After 5 days, the number of the surviving insects was examined, and the controlling value was calculated by the following equation. The Present compound showed 100% of control effects.

Controlling value (%)=$\{1-(Cb \times Tai)/(Cai \times Tb)\} \times 100$ wherein the symbols in the equation represent the following meanings.

Cb: Number of the test insects in untreated group;
Cai: Number of the surviving insects at the time of the investigation in untreated group;
Tb: Number of the test insects in treated group;
Tai: Number of the surviving insects at the time of the investigation in treated group Here the "untreated group" represents a group where a similar treatment procedure to that of the treated group except not using the Present compound is done.

INDUSTRIAL APPLICABILITY

The Present compound has control effects against pests, especially Lepidoptera pests, and thus is useful as an active ingredient of an agent for controlling pests.

The invention claimed is:
1. A compound represented by formula (1)

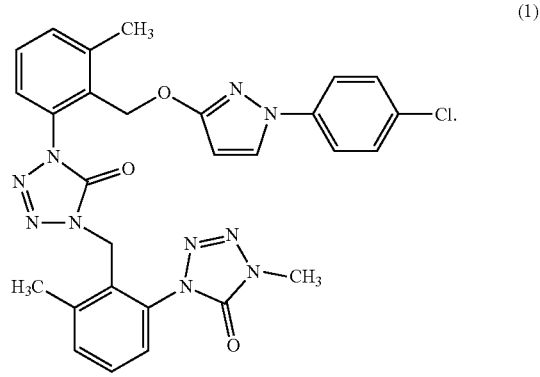 [SMILES: Cc1cccc(-n2nnn(C)c2=O)c1Cn1nnn(-c2cccc(C)c2COc2ccn(-c3ccc(Cl)cc3)n2)c1=O]

(1)

2. An agent for controlling a pest comprising the compound according to claim 1 and a carrier.
3. A method for controlling a pest which comprises applying an effective amount of the compound according to claim 1 to a pest or a habitat where a pest lives.

* * * * *